United States Patent
Vachher et al.

(10) Patent No.: US 10,754,869 B2
(45) Date of Patent: Aug. 25, 2020

(54) MANAGING DATA FORMAT OF DATA RECEIVED FROM DEVICES IN AN INTERNET OF THINGS NETWORK

(71) Applicant: HCL Technologies Limited, Noida, Uttar Pradesh (IN)

(72) Inventors: Harsha Vachher, Noida (IN); Monika Prashar, Noida (IN); Vishal Chaudhary, Sunnyvale, CA (US)

(73) Assignee: HCL Technologies Limited, Noida, Uttar Pradesh ( * ) Notice: Subject to any disclaimer, the term of this patent is extended or adjusted under 35 U.S.C. 154(b) by 155 days.

(21) Appl. No.: 15/610,547

(22) Filed: May 31, 2017

(65) Prior Publication Data
US 2017/0351723 A1    Dec. 7, 2017

(30) Foreign Application Priority Data
Jun. 3, 2016    (IN) .............................. 201611019129

(51) Int. Cl.
| | |
|---|---|
| *G06F 16/00* | (2019.01) |
| *G06F 16/25* | (2019.01) |
| *G16H 10/60* | (2018.01) |
| *G06F 21/44* | (2013.01) |
| *G06F 16/245* | (2019.01) |

(52) U.S. Cl.
CPC ............ *G06F 16/258* (2019.01); *G06F 21/44* (2013.01); *G16H 10/60* (2018.01); *G06F 16/245* (2019.01)

(58) Field of Classification Search
CPC .. G06F 11/1004; G06F 3/0619; G06F 3/0659; G06F 3/0683; G06F 16/245; G06F 21/44; G06F 21/6245; G06F 16/258
See application file for complete search history.

(56) References Cited

U.S. PATENT DOCUMENTS

| | | | |
|---|---|---|---|
| 2015/0237071 A1* | 8/2015 | Maher | ...................... H04W 4/70 726/1 |
| 2017/0091277 A1* | 3/2017 | Zoch | ................. G06F 17/30554 |
| 2017/0126578 A1* | 5/2017 | Amulothu | ............... H04L 67/10 |
| 2017/0270563 A1* | 9/2017 | Soni | ................... G06Q 30/0255 |

FOREIGN PATENT DOCUMENTS

| | | |
|---|---|---|
| CN | 102355682 A | 2/2012 |
| CN | 202522715 U | 11/2012 |
| WO | 2014136401 A1 | 9/2014 |

* cited by examiner

*Primary Examiner* — Dinku W Gebresenbet
(74) *Attorney, Agent, or Firm* — HM Law Group LLP; Vanintheran Moodley

(57) ABSTRACT

The present disclosure relates to system(s) and method(s) for storing sensor data received from a device connected an Internet of Things (IoT) network. The system may store one or more record tables corresponding to one or more devices connected in an Internet of Things (IoT) network, in a database. Further, the system may receive a modification request from a device connected in the Internet of Things (IoT) network, wherein the modification request comprises a unique identification number corresponding to the device and a sensor configuration data. Further, the system may modify a table structure of a record table corresponding to the device to generate a modified table structure, based on the modification request. Further, the system may execute a programmed instruction stored in the memory to store the sensor data received from the device, in the record table, based on the modified table structure.

9 Claims, 5 Drawing Sheets

MANAGING DATA FORMAT OF DATA RECEIVED FROM DEVICES IN AN INTERNET OF THINGS NETWORK

CROSS-REFERENCE TO RELATED APPLICATIONS AND PRIORITY

The present application claims priority from Indian Patent Application No. 201611019129 filed on 3 Jun. 2016, the entirety of which is hereby incorporated by reference.

TECHNICAL FIELD

The present disclosure in general relates to the field of Internet of Things. More particularly, the present invention relates to managing data captured from device in an Internet of Things (IoT) network.

BACKGROUND

Internet of Things (IoT) is nowadays used to fuse the physical and digital worlds by bringing different concepts and technical components together. Nowadays, IoT networks are used to create a seamless network of billions of wireless identifiable objects that communicate with one another through wired or wireless communication means. The era of IoT has lead to the creation of a new ecosystem in which smart devices are enabled to adapt to their respective environments, self-configure, self-maintain and self-repair.

Modern IoT devices provide limited support for the integration of third-party peripherals. In order to solve this problem, plug-and-play (PnP) devices are now being developed which include hardware and software components. PnP provides support for automatic integration of third-party peripherals. The PnP are constructed by stacking together various hardware modules including power sources, processing units and sensors. The main processing unit automatically identifies all the attached modules and adjusts own operation accordingly. The complete modularity of the PnP devices allows users to choose the required functionality from different sensor modules.

With the introduction of PnP IoT devices existing IoT ecosystem need changes to leverage the benefits of such devices. The current IoT ecosystem is inefficient to leverage the benefits of PnP devices in terms of platform communication and service offerings.

SUMMARY

This summary is provided to introduce aspects related to systems and methods for storing sensor data received from a device connected an Internet of Things (IoT) network and the aspects are further described below in the detailed description. This summary is not intended to identify essential features of the claimed subject matter nor is it intended for use in determining or limiting the scope of the claimed subject matter.

In one embodiment, a system for storing sensor data received from a device connected an Internet of Things (IoT) network is illustrated. The system comprises a processor coupled to a memory, wherein the processor is configured to execute programmed instructions stored in the memory. The processor may execute a programmed instruction stored in the memory to store one or more record tables corresponding to one or more devices connected in an Internet of Things (IoT) network, in a database. In one embodiment, each record table is assigned with a unique identification number corresponding to a device of the one or more devices, wherein a table structure of the record table comprises one or more columns configured to maintain sensor data received from one or more sensors connected to the device of the one or more device. Further, the processor may execute a programmed instruction stored in the memory to receive a modification request from a device connected in the Internet of Things (IoT) network, wherein the modification request comprises a unique identification number corresponding to the device and a sensor configuration data corresponding to a sensor added to the device or removed from the device. Further, the processor may execute a programmed instruction stored in the memory to modify a table structure of a record table corresponding to the device to generate a modified table structure, based on the modification request. In one embodiment, the modified table structure of a record table is generated by adding new column or deleting existing columns of the table structure, based on the sensor configuration data. Further, the processor may execute a programmed instruction stored in the memory to store the sensor data received from the device, in the record table, based on the modified table structure.

In one embodiment, a method for storing sensor data received from a device connected an Internet of Things (IoT) network is illustrated. The method may comprise storing one or more record tables corresponding to one or more devices connected in an Internet of Things (IoT) network, in a database. In one embodiment, each record table is assigned with a unique identification number corresponding to a device of the one or more devices, wherein a table structure of the record table comprises one or more columns configured to maintain sensor data received from one or more sensors connected to the device of the one or more device. The method may further comprise receiving a modification request from a device connected in the Internet of Things (IoT) network, wherein the modification request comprises a unique identification number corresponding to the device and a sensor configuration data corresponding to a sensor added to the device or removed from the device. The method may further comprise modifying a table structure of a record table corresponding to the device to generate a modified table structure, based on the modification request. In one embodiment, the modified table structure of a record table is generated by adding new column or deleting existing columns of the table structure, based on the sensor configuration data. The method may further comprise storing the sensor data received from the device, in the record table, based on the modified table structure.

In one embodiment, a non-transitory computer readable medium embodying a program executable in a computing device for storing sensor data received from a device connected an Internet of Things (IoT) network is illustrated. The program comprises a program code for storing one or more record tables corresponding to one or more devices connected in an Internet of Things (IoT) network, in a database. In one embodiment, each record table is assigned with a unique identification number corresponding to a device of the one or more devices, wherein a table structure of the record table comprises one or more columns configured to maintain sensor data received from one or more sensors connected to the device of the one or more device. The program comprises a program code for receiving a modification request from a device connected in the Internet of Things (IoT) network, wherein the modification request comprises a unique identification number corresponding to the device and a sensor configuration data corresponding to a sensor added to the device or removed from the device. The program comprises a program code for modifying a table structure of a record table corresponding to the device to generate a modified table structure, based on the modification request. In one embodiment, the modified table structure of a record table is generated by adding new column or deleting existing columns of the table structure, based on the sensor configuration data. The program comprises a program code for storing the sensor data received from the device, in the record table, based on the modified table structure.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Figure 1:
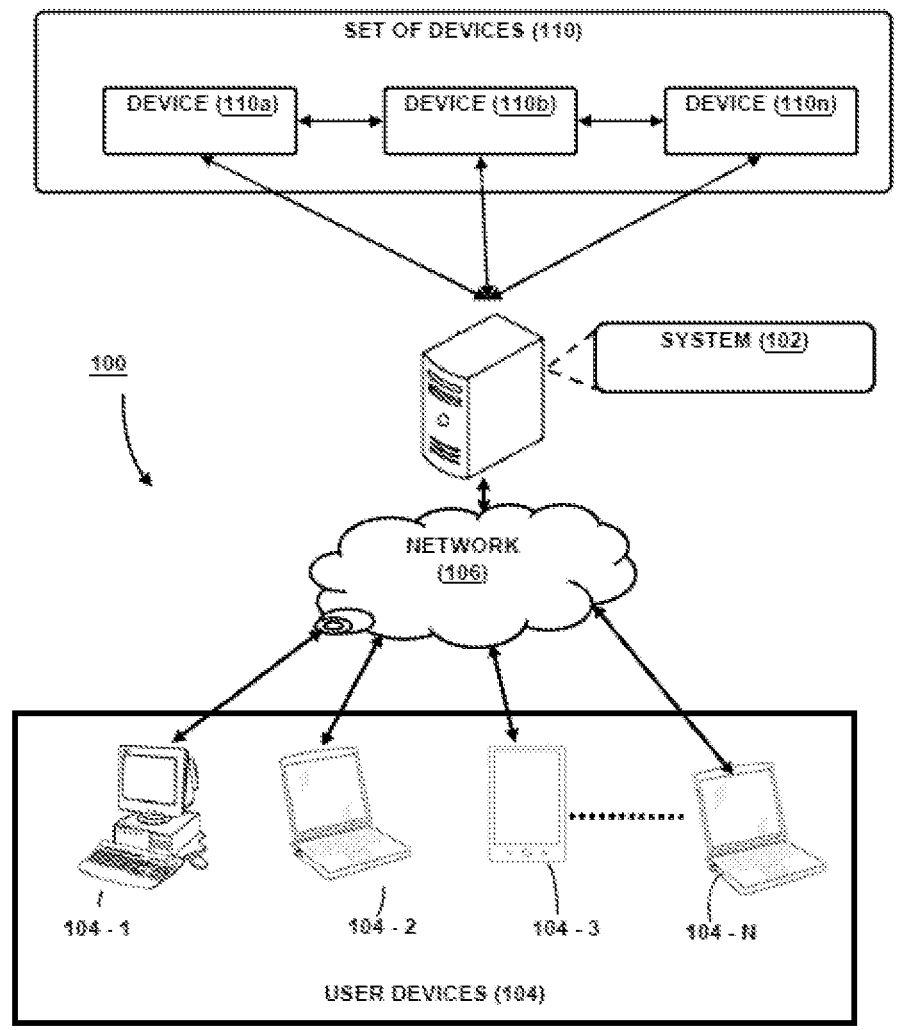
FIG. 1 illustrates a network implementation of a system for storing sensor data received from a device connected an Internet of Things (IoT) network, in accordance with an embodiment of the present subject matter.

The present subject matter relates to a system for storing sensor data received from a device connected an Internet of Things (IoT) network. The system is configured to store one or more record tables corresponding to one or more devices connected in an Internet of Things (IoT) network, in a database. In one embodiment, each record table is assigned with a unique identification number corresponding to a device of the one or more devices, wherein a table structure of the record table comprises one or more columns configured to store sensor data received from one or more sensors connected to the device of the one or more device.

In one embodiment, the record table may be generated after receiving a connection request and the table structure from the device, wherein each column in the table structure is assigned with a data type and a data attribute corresponding to a sensor of the one or more sensors. The data type comprises an integer, a float, a text, and a double, and wherein the data attributes comprise temperature, humidity, speed, acceleration, direction, and proximity. Once the request is received, in the next step, a record table is generated based on the connection request and the table structure. Further, the system is configured to assigning the unique identification number to the record table. Once the unique identification number is assigned, in the next step, the unique identification number is transmitted to the device for future communication.

The system is further configured for receiving a modification request from a device connected in the Internet of Things (IoT) network, wherein the modification request comprises a unique identification number corresponding to the device and a sensor configuration data corresponding to a sensor added to the device or removed from the device. The method may further comprise modifying a table structure of a record table corresponding to the device to generate a modified table structure, based on the modification request. In one embodiment, the modified table structure of a record table is generated by adding new column or deleting existing columns of the table structure, based on the sensor configuration data. The method may further comprise storing the sensor data received from the device, in the record table, based on the modified table structure.

In the existing art, IoT based PnP systems are not equipped to support PnP devices where data format is not constant and can't be defined at the time of provisioning itself. In the PnP systems as a new sensor module is added to main controller, device format is updated. If we try to Provision PnP devices with existing system, we need to re-register every time there is change in data format. Due to this different device IDs are generated for same device and as a result historical data for the device is lost. As IoT is all about data and data processing, losing data due to change in device ID may lead to huge amount of losses.

To address this problem, the system is configured to assign unique identification number and a table structure during provisioning/registration of each device with the system. The table structure of the record table corresponding to the device may be changed based on the change in the sensors attached to the device, without re-registration to prevent any data losses. The present system allows flexibility to change device data format dynamically even after the provisioning process is completed. Further, the system is configured to modify storage as per change in device data format at run-time.

While aspects of described system and method for storing sensor data received from a device connected an Internet of Things (IoT) network may be implemented in any number of different computing systems, environments, and/or configurations, the embodiments are described in the context of the following exemplary system.

Referring now to FIG. 1, a network implementation 100 of a system 102 for storing sensor data received from a device connected an Internet of Things (IoT) network is disclosed. Although the present subject matter is explained considering that the system 102 is implemented on a server, it may be understood that the system 102 may also be implemented in a variety of computing systems, such as a laptop computer, a desktop computer, a notebook, a workstation, a mainframe computer, a server, a network server, and the like. In one implementation, the system 102 may be implemented in a cloud-based environment. It will be understood that the system 102 may be accessed by a primary user through one or more user devices 104-1, 104-2 . . . 104-N, collectively referred to as user devices 104 hereinafter, or applications residing on the user devices 104. Examples of the user devices 104 may include, but are not limited to, a portable computer, a personal digital assistant, a handheld device, and a workstation, file server, version control servers, bugs tracking servers. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Further, the system 102 is connected to one or more devices hereafter referred to as a set of devices 110. In one embodiment, the set of devices 110 are connected to the system 102 through an internet of things network. In one embodiment, the set of devices 110 are configured to transmit sensor data captured from one or more sensors attached to the set of devices 110. Further, the system is configured maintain the sensor data captured from each device of the set of devices in a record table. Furthermore, the system is configured to modify the table structure of the record table based on modification brought to the sensors attached to the device of the set of devices 110. The process of storing sensor data received from a device connected an Internet of Things (IoT) network is further elaborated with respect to FIG. 2.

Figure 2:
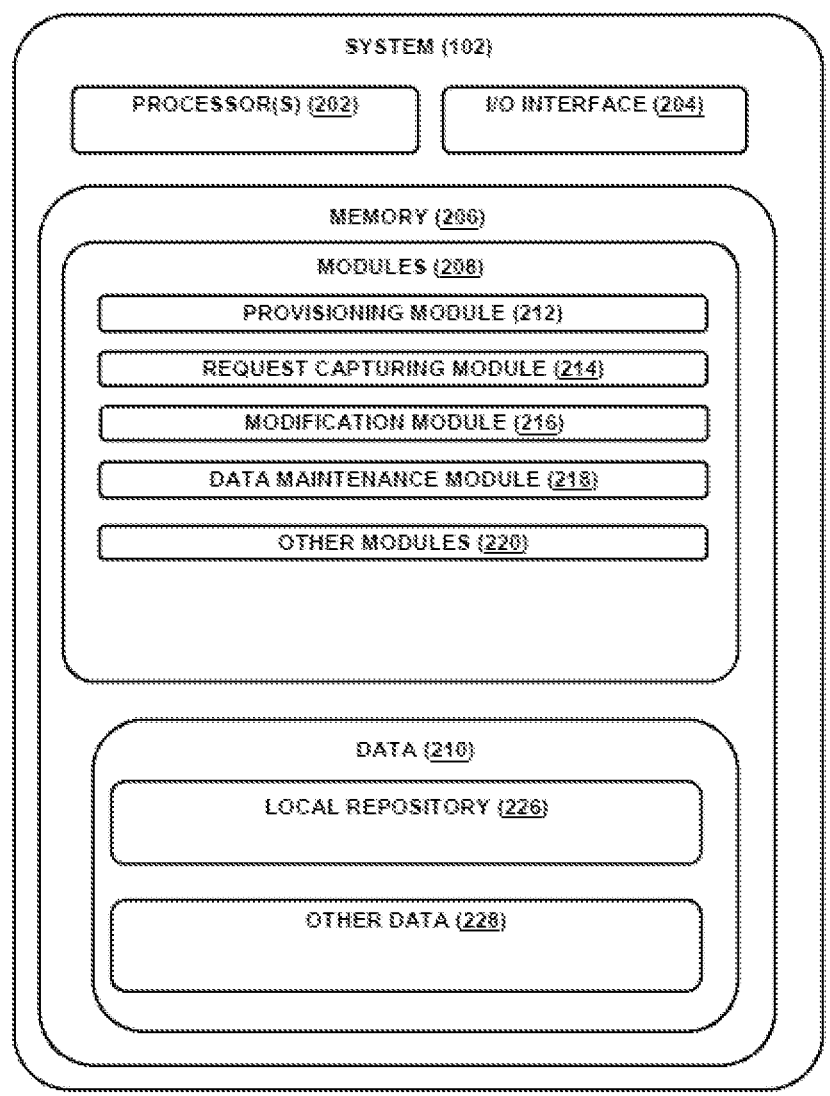
FIG. 2 illustrates the system for storing sensor data received from a device connected an Internet of Things (IoT) network, in accordance with an embodiment of the present subject matter.

Referring now to FIG. 2, the system 102 is illustrated in accordance with an embodiment of the present subject matter. In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with a user directly or through the user devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208 and data 210.

The modules 208 include routines, programs, objects, components, data structures, etc., which perform particular tasks, functions or implement particular abstract data types.

In one implementation, the modules 208 may include a provisioning module 212, a request capturing module 214, a modification module 216, a data maintenance module 218, and other modules 220. The other modules 220 may include programs or coded instructions that supplement applications and functions of the system 102. The data 210, amongst other things, serves as a repository for storing data processed, received, and generated by one or more of the modules 208. The data 210 may also include a local repository 226, and other data 228. The local repository 226 is configured to store the record table corresponding to each device from the set of devices 110 that are generated by the provisioning module 212.

In one implementation, the provisioning module 212 is configured to store one or more record tables corresponding to the set of device 110 in an Internet of Things (IoT) network, in the local repository 226. In one embodiment, the provisioning module 212 is configured to assign each record table with a unique identification number corresponding to a device of the one or more devices. In one embodiment, a table structure of the record table comprises one or more columns configured to maintain sensor data received from one or more sensors connected to the device of the set of device 110.

In one embodiment, the record table for a device may be generated by the provisioning module 212 after receiving a connection request and the table structure from the device of the set of device 110. In one embodiment, the provisioning module 212 may assign each column in the table structure with a data type and a data attribute corresponding to a sensor of the one or more sensors attached to the device. The data type comprises an integer, a float, a text, and a double. The selection of the data type corresponding to the column is based on the type and size of data received from the sensor corresponding to the column. For example, if a speedometer sensor is connected to the device, then the data type selected for the column corresponding to the sensor may be integer. However, in case of a temperature sensor, the data type may be float.

Further, the data attributes comprise temperature, humidity, speed, acceleration, direction, and proximity. The data attribute defines the type of information collected from the sensor. Once the request is received, in the next step, a record table is generated by the provisioning module 212, based on the connection request and the table structure. Further, the provisioning module 212 is configured to assigning the unique identification number to the record table. Once the unique identification number is assigned, in the next step, the unique identification number is transmitted to the device for future communication.

Further, the request capturing module 214 is configured to receive a modification request from a device connected in the Internet of Things (IoT) network. The modification request may comprise a unique identification number corresponding to the device and a sensor configuration data corresponding to a sensor added to the device or removed from the device. The request capturing module 214 is configured to analyse the request and fetch information corresponding to the record table associated with the unique identification number in the request.

Further, the modification module 216 is configured to modify the table structure of the record table corresponding to the device to generate a modified table structure, based on the modification request. In one embodiment, the modified table structure of a record table is generated by adding new column or deleting existing columns of the table structure, based on the sensor configuration data in the modification request. For example, if a new temperature sensor is added to the device, then the information associated with the new temperature sensor in the form of sensor configuration data is transmitted to the modification module 216. The modification module 218 in response adds a column to the record table for storing data captured from the new temperature sensor.

In one embodiment, once the table structure is updated to generate modified table structure, in the next step the data maintenance module 218 is configured to store the sensor data received from the device, in the record table, based on the modified table structure. The method for storing sensor data received from a device connected an Internet of Things (IoT) network is further illustrated with respect to the block diagram of FIG. 3.

Figure 3:
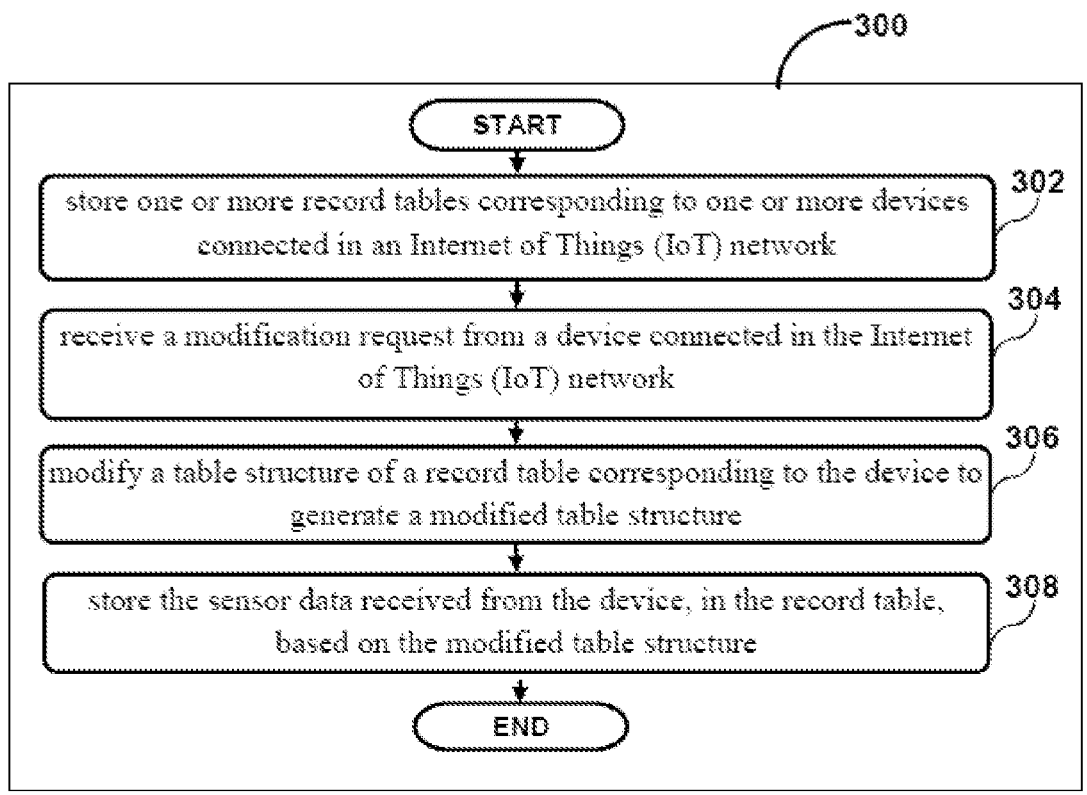
FIG. 3 illustrates a flow diagram for storing sensor data received from a device connected an Internet of Things (IoT) network, in accordance with an embodiment of the present subject matter.

Referring now to FIG. 3, a method 300 for storing sensor data received from a device connected an Internet of Things (IoT) network is disclosed, in accordance with an embodiment of the present subject matter. The method 300 may be described in the general context of computer executable instructions. Generally, computer executable instructions can include routines, programs, objects, components, data structures, procedures, modules, functions, and the like, that perform particular functions or implement particular abstract data types. The method 300 may also be practiced in a distributed computing environment where functions are performed by remote processing devices that are linked through a communications network. In a distributed computing environment, computer executable instructions may be located in both local and remote computer storage media, including memory storage devices.

The order in which the method 300 is described is not intended to be construed as a limitation, and any number of the described method blocks can be combined in any order to implement the method 300 or alternate methods. Additionally, individual blocks may be deleted from the method 300 without departing from the spirit and scope of the subject matter described herein. Furthermore, the method 300 can be implemented in any suitable hardware, software, firmware, or combination thereof. However, for ease of explanation, in the embodiments described below, the method 300 may be considered to be implemented in the above described system 102.

At block 302, the provisioning module 212 is configured to store one or more record tables corresponding to the set of device 110 in an Internet of Things (IoT) network, in the local repository 226. Further, the provisioning module 212 is configured to assign each record table with a unique identification number corresponding to a device of the one or more devices. In one embodiment, a table structure of the record table comprises one or more columns configured to maintain sensor data received from one or more sensors connected to the device of the set of device 110.

In one embodiment, the record table for a device may be generated by the provisioning module 212 after receiving a connection request and the table structure from the device of the set of device 110. In one embodiment, the provisioning module 212 may assign each column in the table structure with a data type and a data attribute corresponding to a sensor of the one or more sensors attached to the device. The data type comprises an integer, a float, a text, and a double. The selection of the data type corresponding to the column is based on the type and size of data received from the sensor corresponding to the column. For example, if a speedometer sensor is connected to the device, then the data type selected for the column corresponding to the sensor may be integer. However, in case of a temperature sensor, the data type may be float.

Further, the data attributes comprise temperature, humidity, speed, acceleration, direction, and proximity. The data attribute defines the type of information collected from the sensor. Once the request is received, in the next step, a record table is generated by the provisioning module 212, based on the connection request and the table structure. Further, the provisioning module 212 is configured to assigning the unique identification number to the record table. Once the unique identification number is assigned, in the next step, the unique identification number is transmitted to the device for future communication.

At block 304, the request capturing module 214 is configured to receive a modification request from a device connected in the Internet of Things (IoT) network. The modification request may comprise a unique identification number corresponding to the device and a sensor configuration data corresponding to a sensor added to the device or removed from the device. The request capturing module 214 is configured to analyse the request and fetch information corresponding to the record table associated with the unique identification number in the request.

At block 306, the modification module 216 is configured to modify the table structure of the record table corresponding to the device to generate a modified table structure, based on the modification request. In one embodiment, the modified table structure of a record table is generated by adding new column or deleting existing columns of the table structure, based on the sensor configuration data in the modification request. For example, if a new temperature sensor is added to the device, then the information associated with the new temperature sensor in the form of sensor configuration data is transmitted to the modification module 216. The modification module 218 in response adds a column to the record table for storing data captured from the new temperature sensor.

At block 308, once the table structure is updated to generate modified table structure, in the next step the data maintenance module 218 is configured to store the sensor data received from the device, in the record table, based on the modified table structure. The format of the modification request is further explained with respect to FIG. 4.

Figure 4:
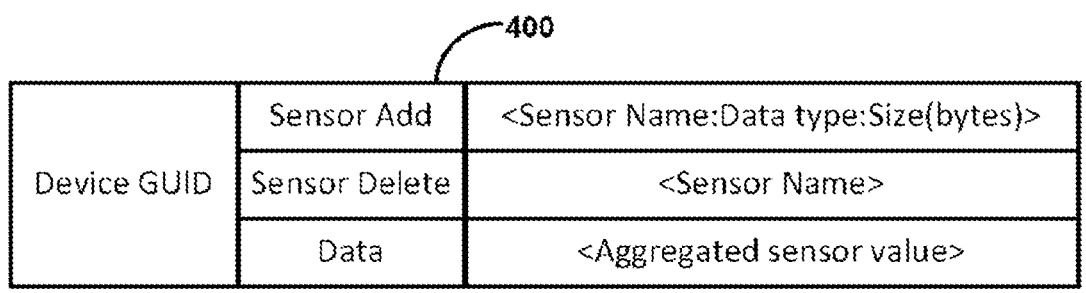
FIG. 4 illustrates format of a modification request for modifying table structure of a record table, in accordance with an embodiment of the present subject matter.

FIG. 4 represents format of the modification request for modifying the table structure of the record table. The request comprises a unique identification number also referred to as Device GUID. The Device GUID uniquely identifies device and is shared during enrolment process. Further, the modification request comprises action parameter comprising sensor add, sensor delete, and sensor data. Based on the action parameter the modification module 216 identifies whether the modification request is for adding new sensor data format, or existing sensor removed or aggregated sensor value and takes action based on the same.

Further, the third parameter contains information corresponding to the action parameter. If the action parameter is for adding new sensor, the third parameter contains data format and data size corresponding to the new sensor. If the action parameter is for removing existing sensor, the third parameter contains sensor name to be removed from the record table. If the action parameter is for adding data to the record table, the third parameter contains aggregated sensor values separated by comma to be added to the record table.

Figure 5:
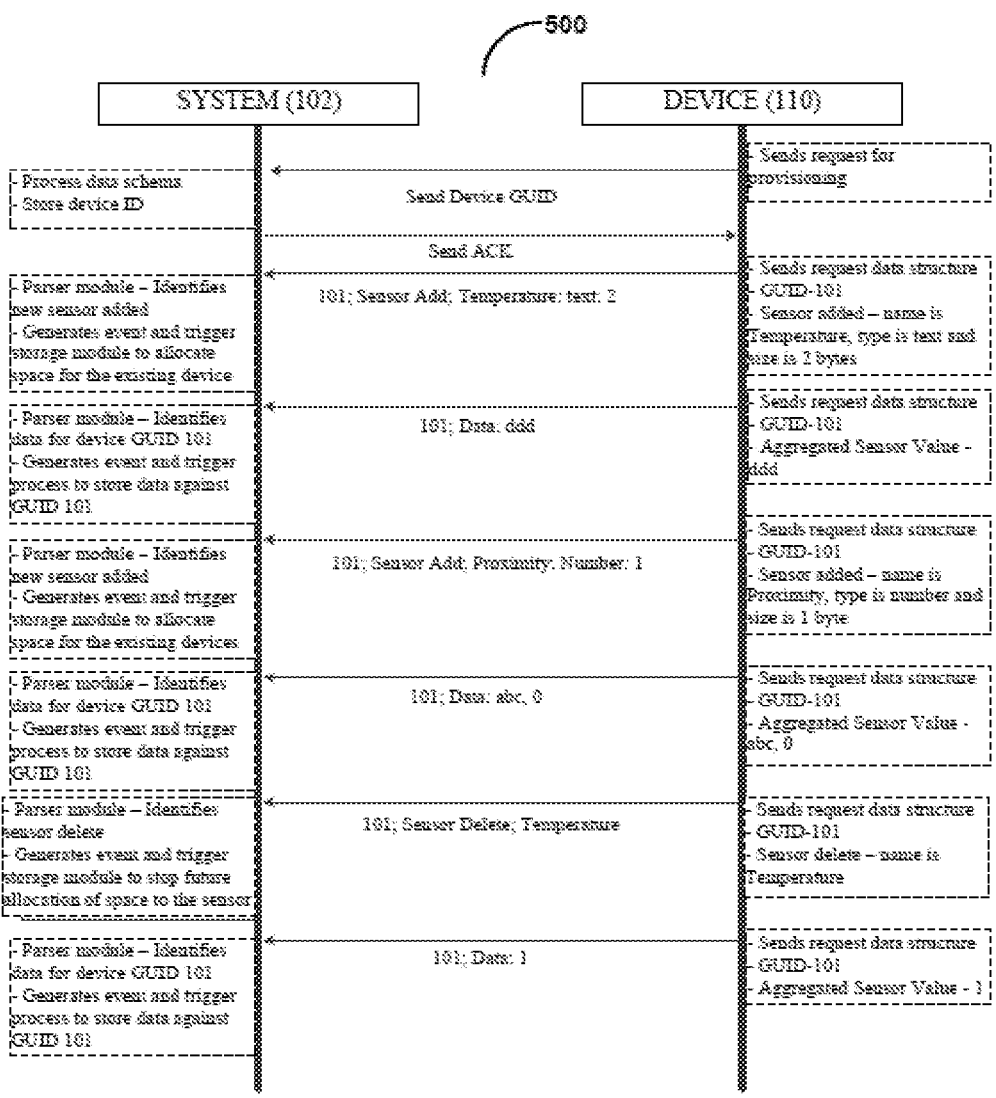
FIG. 5 illustrates a sequence diagram detailing the steps for provisioning a device in the IoT network and modifying the structure of the record table, in accordance with an embodiment of the present subject matter.

Referring now to FIG. 5, a sequence diagram detailing the different steps involved in provisioning a device in the IoT network and modifying the structure of the record table corresponding to the record table based on adding or deleting sensors is disclosed.

Although implementations for methods and systems for storing sensor data received from a device connected an Internet of Things (IoT) network has been described, it is to be understood that the appended claims are not necessarily limited to the specific features or methods described. Rather, the specific features and methods are disclosed as examples of implementations for storing sensor data received from a device connected an Internet of Things (IoT) network.

We claim:

1. A method for storing sensor data received from a device connected to an Internet of Things (IoT) network, the method comprising:
    storing, by a processor, one or more record tables corresponding to one or more devices connected in an Internet of Things (IoT) network, wherein each record table is assigned with a unique identification number corresponding to the device of the one or more devices, and wherein a table structure of the record table comprises one or more columns configured to maintain sensor data received from one or more sensors connected to the device of the one or more devices;
    receiving, by the processor, a modification request from the device connected in the Internet of Things (IoT) network, wherein the modification request comprises the unique identification number corresponding to the device and a sensor configuration data corresponding to a sensor added to the device or removed from the device;
    modifying, by the processor, the table structure of the record table corresponding to the device to generate a modified table structure, based on the modification request, wherein the modified table structure of the record table is generated by adding new column or deleting existing columns of the table structure, based on the sensor configuration data, to provide a Plug and Play (PnP) environment; and
    storing, by the processor, the sensor data received from the device, in the record table, based on the modified table structure.

2. The method of claim 1, wherein the one or more record tables are maintained in a database.

3. The method of claim 1, wherein the method further comprising
    receiving, by a processor, a connection request and the table structure from the device;
    generating, by the processor, a record table based on the connection request and the table structure;
    assigning, by the processor, the unique identification number to the record table; and
    transmitting, by the processor, the unique identification number to the device.

4. The method of claim 1, wherein each column in the table structure is assigned with a data type and a data attribute corresponding to a sensor of the one or more sensors, wherein the data type comprises an integer, a float, a text, and a double, and wherein the data attributes comprise temperature, humidity, speed, acceleration, direction, and proximity.

5. A system for storing sensor data received from a device connected to an Internet of Things (IoT) network, the system comprising:
    a memory; and
    a processor connected to the memory, wherein the processor is configured to execute programmed instructions stored in the memory to:
        store one or more record tables corresponding to one or more devices connected in an Internet of Things (IoT) network, wherein each record table is assigned with a unique identification number corresponding to the device of the one or more devices, and wherein a table structure of the record table comprises one or more columns configured to maintain sensor data received from one or more sensors connected to the device of the one or more devices;
        receive a modification request from the device connected in the Internet of Things (IoT) network, wherein the modification request comprises the unique identification number corresponding to the device and a sensor configuration data corresponding to a sensor added to the device or removed from the device;
        modify the table structure of the record table corresponding to the device to generate a modified table structure, based on the modification request, wherein the modified table structure of the record table is generated by adding new column or deleting existing columns of the table structure, based on the sensor configuration data, to provide a Plug and Play (PnP) environment; and
        store the sensor data received from the device, in the record table, based on the modified table structure.

6. The system of claim 5, wherein the one or more record tables are maintained in a database.

7. The system of claim 5, further configured to:
    receive a connection request and the table structure from the device;
    generate a record table based on the connection request and the table structure;
    assign the unique identification number to the record table; and
    transmit the unique identification number to the device.

8. The system of claim 5, wherein each column in the table structure is assigned with a data type and a data attribute corresponding to a sensor of the one or more sensors, wherein the data type comprises an integer, a float, a text, and a double, and wherein the data attributes comprise temperature, humidity, speed, acceleration, direction, and proximity.

9. A non-transitory computer readable medium embodying a program executable in a computing device for storing sensor data received from a device connected to an Internet of Things (IoT) network, the computer program product comprising:
    a program code for storing one or more record tables corresponding to one or more devices connected in an Internet of Things (IoT) network, wherein each record table is assigned with a unique identification number corresponding to the device of the one or more devices, and wherein a table structure of the record table comprises one or more columns configured to maintain sensor data received from one or more sensors connected to the device of the one or more devices;
    a program code for receiving a modification request from the device connected in the Internet of Things (IoT) network, wherein the modification request comprises the unique identification number corresponding to the device and a sensor configuration data corresponding to a sensor added to the device or removed from the device;

a program code for modifying the table structure of the record table corresponding to the device to generate a modified table structure, based on the modification request, wherein the modified table structure of the record table is generated by adding new column or deleting existing columns of the table structure, based on the sensor configuration data, to provide a Plug and Play (PnP) environment; and a program code for storing the sensor data received from the device, in the record table, based on the modified table structure.

* * * * *